United States Patent [19]

Chapman et al.

[11] 4,174,391
[45] Nov. 13, 1979

[54] SPIRAMYCIN ESTERS

[75] Inventors: Robert F. Chapman, Benfleet; David D. Jackson, Wickford; Glyn E. Lee, Thorpe Bay, all of England

[73] Assignee: May & Baker Limited, Essex, England

[21] Appl. No.: 857,999

[22] Filed: Dec. 6, 1977

[30] Foreign Application Priority Data

Dec. 8, 1976 [GB] United Kingdom ............... 51257/76

[51] Int. Cl.$^2$ ..................... A61K 31/70; C07G 11/00
[52] U.S. Cl. ................................. 424/180; 536/17 R
[58] Field of Search .................... 536/17, 10; 424/123, 424/180

[56] References Cited

U.S. PATENT DOCUMENTS

| | | | |
|---|---|---|---|
| 3,000,786 | 9/1961 | Wettstein et al. | 536/17 |
| 3,795,669 | 3/1974 | Fujimoto et al. | 536/17 |

FOREIGN PATENT DOCUMENTS

| | | | |
|---|---|---|---|
| 785191 | 10/1957 | United Kingdom | 536/17 |
| 796311 | 6/1958 | United Kingdom | 536/17 |

Primary Examiner—Johnnie R. Brown
Assistant Examiner—Blondel Hazel
Attorney, Agent, or Firm—Stevens, Davis, Miller & Mosher

[57] ABSTRACT

The spiramycin derivatives of the formula:

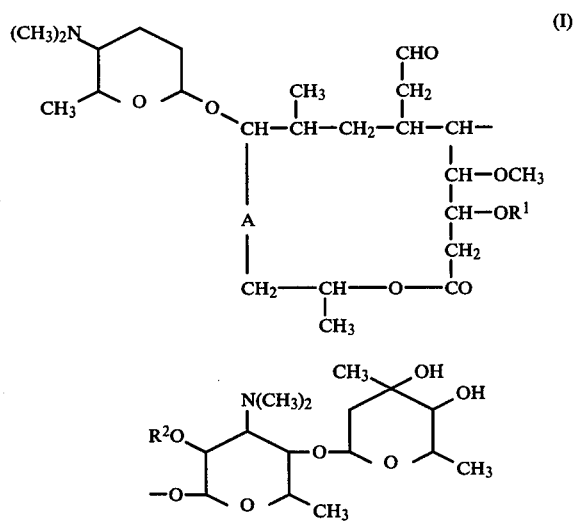

wherein $R^1$ represents acetyl, propionyl or hydrogen, A represents butenylene or butadienylene (wherein any double bonds present in A are trans), and $R^2$ represents a group of the formula:

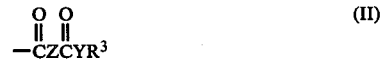

wherein Z represents bivalent saturated or unsaturated alkylene of 1 to 6 carbon atoms, Y represents sulphur or oxygen, and $R^3$ represents alkyl of 1 to 6 carbon atoms, cycloalkyl of 3 to 8 carbon atoms, aryl or aralkyl in which the alkylene moiety is of 1 to 6 carbon atoms and their non-toxic salts possess therapeutic and growth-promoting activity.

29 Claims, No Drawings

SPIRAMYCIN ESTERS

This invention relates to new antibiotics, to processes for preparing them and to compositions containing them.

According to the present invention, there are provided the new spiramycin derivatives of the general formula:

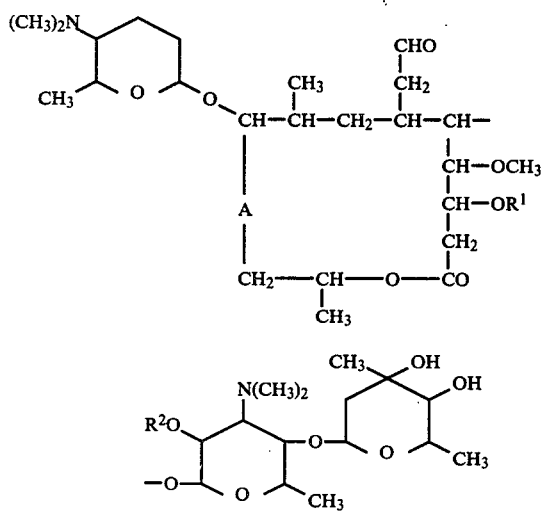

wherein $R^1$ represents an acetyl or propionyl group or, preferably, a hydrogen atom, A represents a butenylene or, preferably, a butadienylene group (wherein any double bonds present in A are trans), and $R^2$ represents a group of the general formula:

[wherein Z represents a bivalent saturated or unsaturated straight- or branched-chain alkylene group containing from 1 to 6 carbon atoms (e.g. ethylene), Y represents a sulphur or, preferably, oxygen atom, and $R^3$ represents a straight- or branched-chain alkyl group containing from 1 to 6, preferably from 1 to 3, carbon atoms, a cycloalkyl group containing from 3 to 8 carbon atoms, an aryl group (e.g. phenyl) or an aralkyl group (e.g. phenylalkyl) in which the alkylene moiety is straight- or branched-chain and contains from 1 to 6 carbon atoms] and mixtures thereof, especially mixtures wherein the compounds of general formula I contained in the said mixture only differ in respect of the symbol $R^1$ and are identical in respect of symbols A and $R^2$, and non-toxic acid addition salts thereof.

Spiramycin derivatives of general formula I wherein $R^2$ represents a group of general formula II in which Z represents an ethylene or trimethylene group, Y represents the oxygen atom and $R^3$ represents a straight-chain alkyl group containing from 1 to 3, carbon atoms, preferably ethyl, are preferred.

By the term "non-toxic acid addition salt" is meant a salt, the anion of which is relatively innocuous to the animal organism when used in therapeutic doses, so that the beneficial properties of the cation are not vitiated by side-effects ascribable to the anion.

In the present specification, wherever reference is made to compounds of general formula I, it is intended to refer also to the said salts, where the context so permits.

As will be apparent to those skilled in the art, the group of general formula II may exhibit chirality as a result of chirality in one or both of the moieties Z and $R^3$. The presence of chirality, as is well known, can lead to isomerism. The present invention includes within its scope all isomers of general formula I arising from the said chirality in groups of general formula II, and mixtures thereof.

According to a feature of the present invention, compounds of general formula I, wherein the symbols $R^1$, A and $R^2$ are as hereinbefore defined, are prepared from compounds of the general formula:

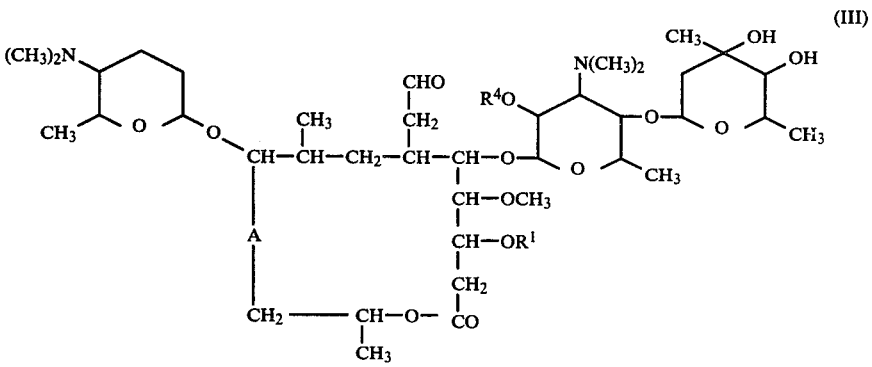

(wherein $R^1$ and A are as hereinbefore defined, and $R^4$ represents a group of the general formula:

wherein Z is as hereinbefore defined) by the application or adaptation of known methods for the preparation of esters from carboxylic acids, for example by reaction with compounds of the general formula:

$$R^3YH \qquad V$$

wherein Y and $R^3$ are as hereinbefore defined.

The reaction is effected in the presence of a compound of the general formula:

(wherein $X^1$ represents a bromine or chlorine atom and $R^5$ represents an alkyl group containing from 1 to 4 carbon atoms) and an acid acceptor, for example a tertiary amine, e.g. triethylamine, preferably at a temperature between −30° C. and +30° C., and preferably in the presence of an anhydrous inert organic solvent, e.g. chloroform.

According to a further feature of the present invention, compounds of general formula I, wherein the symbols $R^1$, A and $R^2$ are as hereinbefore defined, are prepared from compounds of the general formula:

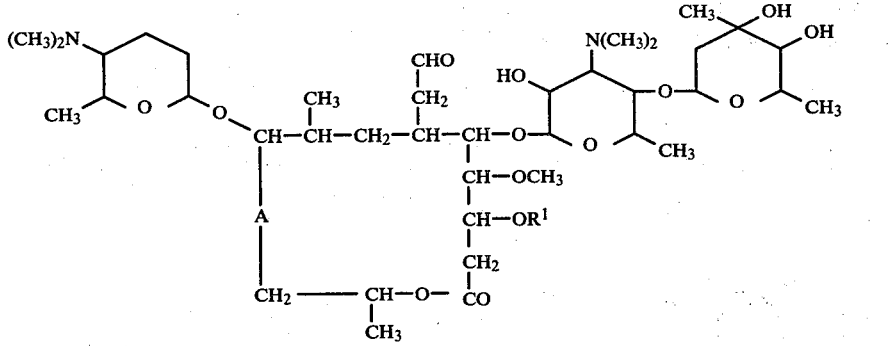

(wherein $R^1$ and A are as hereinbefore defined) by the application or adaptation of known methods for the preparation of esters from alcohols, for example by reaction with compounds of the general formula:

$$X^2OCZCOYR^3 \qquad \text{VIII}$$

wherein $X^2$ represents a bromine or chlorine atom or a group of the general formula:

$$-OCOOR^5 \qquad \text{IX}$$

(wherein $R^5$ is as hereinbefore defined), and Z, Y and $R^3$ are as hereinbefore defined.

The reaction is effected, optionally in the presence of an acid acceptor, for example a tertiary amine, e.g. triethylamine, or an inorganic base, e.g. sodium bicarbonate, preferably in the presence of an anhydrous inert organic solvent, e.g. chloroform or acetone, and preferably at a temperature of from −30° C. to +30° C.

According to a further feature of the present invention, compounds of general formula I, wherein the symbol A represents a trans-butenylene group and the symbols $R^1$ and $R^2$ are as hereinbefore defined, are prepared by the partial reduction of compounds of general formula I, wherein the symbol A represents a butadienylene group (wherein the double bonds are trans) and the symbols $R^1$ and $R^2$ are as hereinbefore defined, by the application or adaptation of known methods, for example by catalytic hydrogenation.

Suitable hydrogenation catalysts include noble metals such as palladium and platinum, and their oxides, optionally supported on, for example, alumina, carbon or barium sulphate.

Non-toxic acid addition salts of the compounds of general formula I may be prepared by the application or adaptation of known methods for the preparation of salts of organic bases, for example by reaction of compounds of general formula I with the appropriate acid in a suitable solvent. The salts may be isolated by lyophilisation of the solution or, if sufficiently insoluble in the reaction medium, by filtration, if necessary after removal of part of the solvent.

Mixtures of compounds of general formula I may be separated into component compounds of general formula I by the application or adaptation of known methods for the separation of antibiotic mixtures, for example by a countercurrent distribution method, for example in a Craig apparatus (A. Weissberger, Technique of Organic Chemistry, Interscience Publishers, New York, Vol. III, p. 286), by chromatography (e.g. on alumina or silica gel), or by fractional crystallisation, for example from an aromatic hydrocarbon solvent, for example benzene.

Compounds of general formula III may be prepared from compounds of general formula VII by the application or adaptation of known methods for the preparation of dicarboxylic acid hemiesters, for example by reaction with compounds of the general formula:

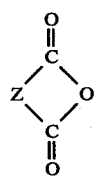

wherein Z is as hereinbefore defined.

The reaction may be effected in the presence of an inert organic solvent, preferably at room temperature and optionally in the presence of a base for example, an alkali metal carbonate or bicarbonate, a tertiary amine or a heterocyclic tertiary base, e.g. pyridine.

Compounds of general formula VIII may be prepared from compounds of general formula V by the application or adaptation of known methods for the preparation of esters from alcohols and thiols, for example by reaction of compounds of general formula V with compounds of general formula X, in a manner similar to that hereinbefore described for the preparation of compounds of general formula III from compounds of general formula VII, followed by the conversion of the hemiesters thus obtained to compounds of general formula VIII by the application or adaptation of known methods for the preparation of acyl halides or mixed acid anhydrides from carboxylic acids.

The compounds of general formula VII, wherein the symbol A represents a butadienylene group (wherein the double bonds are both trans) and the symbol $R^1$ represents a hydrogen atom, an acetyl group or a propionyl group, which are known as spiramycin I, spiramycin II and spiramycin III, respectively, and mixtures thereof may be prepared by the application or adaptation of known methods for the preparation of spiramycins, for example by aerobic cultivation of *Streptomyces ambofaciens* NRRL 2420 or a spiramycin-producing mutant thereof.

The spiramycin usually obtained by fermentation of *Streptomyces ambofaciens* is a mixture of these three spiramycins but it is also possible to obtain each of these spiramycins directly by fermentation, and in particular spiramycin I [see L. Ninet and J. Verrier, Prod. Pharm. 17 (4) 1 (1962)].

Compounds of general formula VII, wherein the symbol A represents a trans-butenylene group and the symbol $R^1$ is as hereinbefore defined, and non-toxic acid addition salts thereof, may be prepared by the partial reduction of spiramycins I, II and III and mixtures thereof and non-toxic acid addition salts thereof, by the application or adaptation of methods hereinbefore described for the reduction of compounds of general formula I, wherein the symbol A represents a butadienylene group (wherein the double bonds are trans) and the symbols $R^1$ and $R^2$ are as hereinbefore defined, for example as described in the specification of British Pat. No. 785191.

By the term "known methods" as used in the present specification is meant methods heretofore used or described in the chemical literature.

The compounds of general formula VII and their non-toxic acid addition salts are antibiotic substances possessing antibacterial properties which make them extremely useful in the treatment of infections due to *Staphylococcus aureus*, and pneumococcal and streptococcal infections, and also, in veterinary medicine in the treatment of mycoplasmosis (a disease known also as infectious sinusitis or air-sacculitis) in turkeys caused primarily by the pleuropneumonia-like organism known as *Mycoplasma gallisepticum*.

The compounds of general formula VII and their non-toxic acid addition salts also possess growth promoting activity which make them extremely useful in improving the growth rate and/or the feed conversion ratio of animals and birds, particularly domestic animals and birds, for example pigs, cattle, e.g. calves, and poultry e.g. chickens and turkeys. Such an improvement in the growth rate of the animals or birds means that they attain the desired weight for example for marketing, in a shorter period of time than is usually necessary, or attain a greater weight over the same period of time. Such an improvement in the feed conversion ratio of animals and birds means that they consume less food to reach a particular weight than similar animals or birds which do not receive a compound of general formula VII or a non-toxic acid addition salt thereof. When administered to poultry, the compounds of general formula VII are also of use in promoting their egg production. The compounds of general formula VII are normally administered to animals and birds in association with a balanced diet.

The compounds of general formula I possess therapeutic and growth promoting activity of a similar type and degree as that of the compounds of general formula VII and, furthermore, they possess the important advantage of being less bitter than the compounds of general formula VII, or even practically tasteless. This advantage is of particular importance in the treatment of children and animals and birds by oral administration of compounds of general formula I.

Although the non-toxic acid addition salts of the compounds of general formula I may lack the advantage of being less bitter than compounds of general formula VII, they are of use in the purification of compounds of general formula I, for example by exploitation of the solubility differences between the salts and the parent bases in water and in organic solvents, by techniques well known to those skilled in the art. The parent bases of general formula I can be regenerated from their salts by known methods, for example by treatment with a mineral base, e.g. aqueous sodium hydroxide solution.

In British patent specification No. 796311 there are disclosed hemiesters formed by spiramycins with dicarboxylic acids of the aliphatic series, which hemiesters are less bitter than the compounds of general formula VII.

Nevertheless, the compounds of general formula I are even less bitter than the compounds disclosed in the said British patent specification No. 796311.

The following compounds of formula I and mixtures thereof are of particular interest:

| | Compound |
|---|---|
| A | 2'-ethyl succinate |
| B | 2'-ethyl glutarate |
| C | 2'-methyl succinate |
| D | 2'-propyl succinate |
| E | 2'-methyl glutarate |
| F | 2'-methyl fumarate |
| G | 2'-S-methyl thiosuccinate |
| H | 2'-cyclohexyl succinate |
| J | 2'-ethyl malonate |
| K | 2'-phenyl succinate |
| L | 2'-methyl (RS)-(3-methyl)succinate |
| M | 2'-(2-phenylethyl) succinate |
| N | 2'-tertiary-butyl succinate |
| O | 2'-isopropyl succinate |
| of spiramycin I; | |
| P | 2'-ethyl succinate of spiramycin mixture; and |
| Q | dihydrochloride of compound A |
| R | dioxalate of compound A |

The letters of the alphabet A to H and J to R are assigned to the compounds for easy reference later in the specification, for example in the following Table.

In experiments on therapeutic activity and biological activity in vitro carried out on compounds of general formula I, the following test results were obtained:

TEST 1—MOUSE TREATED ORALLY

Mice were injected intra-peritoneally with *Staphylococcus aureus* Smith suspended in mucin (0.5 ml). This infection represented approximately 100 times the minimum dose calculated to kill 100% of mice. The mice were each treated orally with 16, 31, 62.5, 125 or 250 mg/kg animal body weight doses of a compound of general formula I. Each mouse was dosed 1, 4, 24, 30 and 48 hours after infection, with the selected dose. The mice were observed for seven days after infection.

The results obtained from a compound of general formula I were compared with the results obtained from spiramycin I used as a standard compound.

The results obtained are shown in Table I (ii) below.

The term "CD50" means the dose calculated to cure 50% of the mice treated.

TEST 2—MOUSE TREATED SUBCUTANEOUSLY

Mice were infected intra-peritoneally with *Staphylococcus aureus* Smith [approximately 100 times the minimum dose lethal to 100% of mice infected] suspended in mucin (0.5 ml). The mice were each treated subcutaneously 1, 4, 24, 30 and 48 hours after infection, with 1.6, 3.1, 6.25, 12.5 or 25 mg/kg animal body weight doses of a compound of general formula I. The mice were observed for seven days after infection.

The results obtained from a compound of general formula I were compared with the results obtained from spiramycin I used as a standard compound. Thus compound A exhibited a CD50 of 17.5 mg/kg animal body weight, while spiramycin I exhibited a CD50 of 5.8 mg/kg animal body weight.

TEST 3—IN VITRO ACTIVITY

For each test compound, a range of concentrations in tryptone soya broth was prepared. Each test-tube containing a different concentration of the test compound within the range was inoculated with the test organism selected from *Staphylococcus aureus* (Oxford) or *Escherichia coli* B (Ennis) (approximately $10^5$ organisms per tube) and after incubation at 37° C., the lowest concentration of test compound within the range required to prevent the growth of the test organism was recorded as the minimum inhibitory concentration for that compound and that organism.

The results obtained are set out in Table I (i) below.

TABLE I

| | (i) In vitro. Minimum inhibitory concentration (μg/ml) | | (ii) Mouse In vivo CD50 (oral) (mg/kg) | |
|---|---|---|---|---|
| Compound | S. aureus (Oxford) | Escherichia coli B (Ennis) | | Spiramycin I |
| A | 1.25 | 62 | 88 | 71 |
| B | 1.25 | 62 | 135 | 71 |
| C | 2.5 | 250 | 62 | 47 |
| D | 2.5 | 250 | 90 | 47 |
| E | 2.5 | 125 | 125 | 79 |
| F | 2.5 | 250 | 125 | 62 |
| G | 2.5 | 500 | 114 | 62 |
| H | 2.5 | 250 | 67 | 41 |
| J | 5 | 250 | 120 | 95 |
| K | 2.5 | 250 | 76 | 41 |
| L | 2.5 | 250 | 58 | 41 |
| M | 2.5 | 250 | 64 | 41 |
| N | 2.5 | 125 | 130 | 79 |
| O | 1.25 | 125 | 96 | 62 |
| P | 5 | 250 | 175 | 110 |
| Spiramycin | 0.62–2.5 | 62–250 | | |

These results demonstrate that the compounds of general formula I possess the same order of activity as the compounds of general formula VII.

The utility of the compounds of general formula I as antibiotics and growth promoters is enhanced by the fact that they are relatively harmless to mammals, as is demonostrated by the following test.

MOUSE TOXICITY

Mice were each treated orally with one of the compounds of general formula I, and they were observed during the next 3 days.

The LD50 figures obtained (doses lethal to 50% of mice treated) are shown in Table II, expressed in mg/kg animal body weight. None of the mice died during the experiment even at doses of 1000 mg/kg animal body weight.

TABLE II

| Compound | LD50 |
|---|---|
| A | >1000 |
| B | >1000 |

The symbol ">" means "greater than" in this specification.

The following Examples illustrate the preparation of the new compounds according to the present invention:

EXAMPLE 1 COMPOUND A

A solution of ethyl 3-chloroformylpropionate (3.2 g) in dry chloroform (50 ml) was added dropwise with stirring to a solution of spiramycin I (15 g) in dry chloroform (100 ml). The temperature was maintained throughout the addition at a temperature of from 0° C. to 10° C. with cooling in an ice bath. The mixture was left for 4 hours at room temperature. The solvent was removed in vacuo and the residue was shaken with aqueous acetic acid solution (100 ml; 1 N). The resulting mixture was extracted with diethyl ether (150 ml). The aqueous layer was separated and was adjusted to about pH 7 by the addition of aqueous sodium hydroxide solution (10 N). The mixture was then extracted with diethyl ether (150 ml) and this ether extract was dried over magnesium sulphate. The diethyl ether was distilled off under reduced pressure to give 2'-ethyl succinate of spiramycin I (4.5 g) in the form of a white solid, m.p. 100°–110° C.

EXAMPLE 2 COMPOUND B

Triethylamine (3 g) and a solution of ethyl 4-chloroformylbutyrate (5.1 g) in dry chloroform (50 ml), the latter in a dropwise manner, were added with stirring to a solution of spiramycin I (24 g) in dry chloroform (100 ml). The temperature was maintained throughout the addition at a temperature of from 0° C. to 10° C. with cooling in an ice bath. The mixture was left for 4 hours at room temperature. The solvent was removed in vacuo and the residue was shaken with aqueous acetic acid solution (100 ml; 1 N). The resulting mixture was extracted with diethyl ether (150 ml). The aqueous layer was separated and was adjusted to about pH 7 by the addition of aqueous sodium hydroxide solution (10 N). The mixture was then extracted with diethyl ether (150 ml) and this ether extract was dried over magnesium sulphate. The diethyl ether was distilled off under reduced pressure to give 2'-ethyl glutarate of spiramycin I (3.0 g) in the form of a white solid, m.p. 87°–95° C.

EXAMPLE 3 COMPOUND C

Triethylamine (1.0 g) and a solution of methyl 3-chloroformylpropionate (1.7 g) in dry chloroform (10 ml), the latter in a dropwise manner, were added with stirring to a solution of spiramycin I (8.4 g) in dry chloroform (100 ml). The mixture was stirred for 3 hours and then the solvent was removed in vacuo. To the resulting residue was added aqueous acetic acid solution (75 ml; 1 N) and diethyl ether (100 ml). The mixture was shaken until the solid dissolved. The aqueous layer was separated and was adjusted to about pH 7 by the addition of aqueous sodium hydroxide solution (10 N). The mixture was then extracted with diethyl ether (100 ml)

and the ether extract was dried over magnesium sulphate. The diethyl ether was distilled off under reduced pressure to give 2'-methyl succinate of spiramycin I (1.0 g) in the form of a white solid, m.p. 108°–118° C.

EXAMPLE 4 COMPOUND D

A solution of propyl 3-chloroformylpropionate (1.8 g) in dry chloroform (10 ml) was added dropwise with stirring to a solution of spiramycin I (8.4 g) in dry chloroform (70 ml). The mixture was stirred for a further 5 hours and then the solvent was removed in vacuo. The residue was dissolved in aqueous acetic acid solution (100 ml; 1 N) and the resulting mixture was extracted with diethyl ether (100 ml). The aqueous layer was separated and was adjusted to about pH 7 by the addition of aqueous sodium hydroxide solution (10 N). The mixture was extracted with diethyl ether (100 ml) and this ether extract was dried over magnesium sulphate. The diethyl ether was distilled off under reduced pressure to give 2'-propyl succinate of spiramycin I (0.7 g) in the form of a white solid, m.p. 88°–96° C.

EXAMPLE 5 COMPOUND E

Triethylamine (1.0 g) and a solution of methyl 4-chloroformylbutyrate (1.65 g) in dry chloroform (20 ml), the latter in a dropwise manner, were added with stirring to a solution of spiramycin I (8.4 g) in dry chloroform (70 ml). The mixture was stirred for a further 3 hours and was left to stand for 17 hours. The reaction mixture was extracted with aqueous acetic acid solution (100 ml; 1 N). The chloroform layer was separated and washed with 5% w/v aqueous sodium carbonate solution (100 ml). The chloroform layer was then dried over magnesium sulphate. The chloroform was distilled off under reduced pressure to give 2'-methyl glutarate of spiramycin I (3.2 g) in the form of a buff coloured solid, m.p. 85°–95° C.

EXAMPLE 6 COMPOUND F

Sodium bicarbonate (8 g) and a solution of methyl trans-3-chloroformylacrylate (2.2 g) in dry acetone (40 ml), the latter in a dropwise manner, were added with stirring to a solution of spiramycin I (8.4 g) in dry acetone (80 ml). The mixture was stirred for a further 3 hours and was left to stand for 17 hours, and then the solid was filtered off. The filtrate was evaporated and the residue was dissolved in ethyl acetate (100 ml). This solution was extracted with aqueous acetic acid solution (75 ml; 1 N). The aqueous layer was separated and extracted with chloroform (2×50 ml). The combined chloroform extracts were washed with water (100 ml) and 5% w/v aqueous sodium bicarbonate solution (100 ml). The chloroform layer was then dried over magnesium sulphate. The chloroform was distilled off under reduced pressure to give 2'-methyl fumarate of spiramycin I (2.7 g), m.p. 105°–115° C.

EXAMPLE 7 COMPOUND G

Triethylamine (1.1 g) and ethyl chloroformate (1.1 g) and a solution of methanethiol (1.0 g) in dry chloroform (50 ml), the latter in a dropwise manner, were added with stirring to a solution of spiramycin I 2'-hemisuccinate (9.4 g) in dry chloroform (80 ml) cooled to −15° C. The temperature was maintained at a temperature of from −15° C. to −10° C. during the addition. The mixture was allowed to warm to room temperature and was left for 18 hours. The solvent was removed by distillation under reduced pressure. Diethyl ether (100 ml) was added to the residue and the insoluble material was filtered off. The filtrate was extracted with aqueous acetic acid solution (100 ml; 1 N). The aqueous layer was separated and was adjusted to about pH 6 by the addition of aqueous sodium hydroxide solution (10 N). The mixture was extracted with diethyl ether (100 ml) and the diethyl ether extract was washed with 5% w/v aqueous sodium bicarbonate solution (100 ml) and dried over magnesium sulphate. The diethyl ether was distilled off under reduced pressure to give 2'-S-methyl thiosuccinate of spiramycin I (1.4 g), m.p. 114°–124° C.

The 2'-succinic acid hemiester of spiramycin I used in the foregoing preparative example was prepared as follows:

Succinic anhydride (6.0 g) was added with stirring to a solution of spiramycin I (50.4 g) in ethyl acetate (600 ml). The mixture was stirred for a further 3 hours and was left for 18 hours at room temperature. The solvent was removed in vacuo and diethyl ether (200 ml) was added to the residue. The solid was filtered off and dried to give 2'-succinic acid hemiester of spiramycin I (38.6 g), m.p. 140°–148° C.

EXAMPLE 8 COMPOUND H

Sodium bicarbonate (4.0 g) and a solution of cyclohexyl 3-chloroformylpropionate (2.4 g) in dry acetone (10 ml), the latter in a dropwise manner, were added with stirring to a solution of spiramycin I (8.4 g) in dry acetone (70 ml). The mixture was stirred for 3 hours and then left for 16 hours. The mixture was filtered and the filtrate was evaporated under reduced pressure. The residue was dissolved in ethyl acetate (70 ml) and the resulting mixture was extracted with aqueous acetic acid solution (75 ml; 0.5 N). The aqueous layer was separated and extracted with chloroform (2×50 ml). The combined chloroform extracts were washed with water (100 ml) and 5% w/v aqueous sodium bicarbonate solution (75 ml), and were dried over magnesium sulphate. The chloroform was evaporated off in vacuo to give 2'-cyclohexyl succinate of spiramycin I (3.4 g), m.p. 90°–100° C.

EXAMPLE 9 COMPOUND J

Sodium bicarbonate (8 g) and a solution of ethyl 2-chloroformylacetate (1.5 g) in dry acetone (20 ml), the latter in a dropwise manner, were added with stirring to a solution of spiramycin I (8.4 g) in dry acetone (75 ml). The stirring was continued for 5 hours and the mixture was then left to stand for 17 hours. The solid was filtered off and the filtrate was evaporated in vacuo. The residue was dissolved in ethyl acetate (100 ml) and this solution was extracted with aqueous acetic acid solution (75 ml; 0.5 N). The aqueous layer was separated and extracted with chloroform (2×50 ml). The chloroform extracts were combined, washed with water (100 ml) and 5% w/v aqueous sodium bicarbonate solution (100 ml), and were dried over magnesium sulphate. The chloroform was distilled off under reduced pressure to give 2'-ethyl malonate of spiramycin I (2.0 g), m.p. 89°–99° C.

EXAMPLE 10 COMPOUND K

Triethylamine (1.5 g) and ethyl chloroformate (1.7 g) were added with stirring to a solution of phenyl hydrogen succinate (2.7 g) in dry chloroform (50 ml), cooled to −15° C. A solution of spiramycin I (8.4 g) in dry chloroform (30 ml) was added dropwise to the resulting mixture, whilst the temperature of the mixture was maintained at −15° C. to −10° C. The mixture was allowed to warm to room temperature and was left for 17 hours. The mixture was evaporated in vacuo, and ethyl acetate (75 ml) and 5% w/v aqueous sodium bicarbonate solution (75 ml) wre added to the residue. The organic layer was separated and extracted with aqueous acetic acid solution (75 ml; 0.5 N). The aqueous layer was then extracted with chloroform (2×50 ml). The combined chloroform extracts were washed with water (100 ml) and 5% w/v aqueous sodium bicarbonate solution (75 ml) and were dried over magnesium sulphate. Evaporation of the chloroform under reduced pressure gave 2'-phenyl succinate of spiramycin I (5.1 g) m.p. 105°–115° C.

EXAMPLE 11 COMPOUND L

Sodium bicarbonate (8 g) and a solution of methyl (RS)-3-chloroformyl-3-methylpropionate (2.5 g) in dry acetone (20 ml), the latter in a dropwise manner, were added with stirring to a solution of spiramycin I (8.4 g) in dry acetone (80 ml). The stirring was continued for 4 hours and the mixture was then left to stand for 18 hours. The solid was filtered off and the filtrate evaporated in vacuo. The residue was dissolved in aqueous acetic acid solution (75 ml; 0.5 N). The resulting mixture was extracted with ethyl acetate (2×50 ml) and then with chloroform (2×5 ml). The combined chloroform extracts were washed with water (100 ml) and 5% w/v aqueous sodium bicarbonate solution (100 ml) and dried over magnesium sulphate. The chloroform was distilled off under reduced pressure to give 2'-methyl (RS)-(3-methyl)succinate of spiramycin I (1.7 g), m.p. 92°–102° C.

EXAMPLE 12 COMPOUND M

Triethylamine (1.1 g) and ethyl chloroformate (1.1 g) were added with stirring to a solution of spiramycin I 2'-hemisuccinate (9.4 g) in dry chloroform (80 ml) cooled to −15° C. A solution of 2-phenylethanol (1.8 g) in dry chloroform (20 ml) was added dropwise whilst the temperature was maintained at −15° C. to −10° C. The mixture was then allowed to warm to room temperature and was left for 18 hours. The solvent was removed under reduced pressure and the residue was dissolved in aqueous acetic acid solution (100 ml; 1 N). The solution was extracted with diethyl ether (100 ml). The aqueous layer was separated and was adjusted to about pH 6 with aqueous sodium hydroxide solution (10 N). The mixture was extracted with diethyl ether (100 ml) and this ether extract was washed with 5% w/v aqueous sodium bicarbonate solution (100 ml) and dried over magnesium sulphate. The diethyl ether was distilled off under reduced pressure to give 2'-(2-phenylethyl) succinate of spiramycin I (2.3 g), m.p. 58°–68° C.

EXAMPLE 13 COMPOUND N

Triethylamine (1.1 g) and ethyl chloroformate (1.1 g) were added with stirring to a solution of spiramycin I 2'-hemisuccinate (9.4 g) in dry chloroform (80 ml) cooled to −15° C. A solution of tertiary-butanol (1.2 ml) in dry chloroform (40 ml) was then added dropwise to the resulting mixture, whilst the temperature was maintained between −15° C. and −10° C. The stirring was continued while the reaction was allowed to warm to room temperature and the mixture was then left to stand for 18 hours. The solvent was removed under reduced pressure and the residue dissolved in aqueous acetic acid solution (100 ml; 1 N). The mixture was extracted with diethyl ether (100 ml). The aqueous layer was separated and was adjusted to about pH 6 with aqueous sodium hydroxide solution (10 N). The mixture was extracted with diethyl ether (100 ml) and this ether extract was washed with 5% w/v aqueous sodium bicarbonate solution (100 ml), and dried over magnesium sulphate. The diethyl ether was distilled off under reduced pressure to give 2'-tertiary-butyl succinate of spiramycin I (0.9 g), m.p. 99°–108° C.

EXAMPLE 14 COMPOUND O

A solution of triethylamine (1.0 g) in dry chloroform (10 ml) and a solution of isopropyl 3-chloroformylpropionate (2.2 g) in dry chloroform (20 ml), the latter in a dropwise manner, were added with stirring to a solution of spiramycin I (8.4 g) in dry chloroform (75 ml). The mixture was stirred for 5 hours and was then left to stand for 18 hours. The solvent was removed under reduced pressure, and aqueous acetic acid solution (100 ml; 1 N) and diethyl ether (100 ml) were added with shaking. The aqueous layer was separated and was adjusted to about pH 6 with aqueous sodium hydroxide solution (10 N). The mixture was extracted with diethyl ether (100 ml) and this ether extract was washed with 5% w/v aqueous sodium bicarbonate solution (100 ml), and dried over magnesium sulphate. The diethyl ether was removed under reduced pressure to give 2'-isopropyl succinate of spiramycin I (1.2 g), m.p. 105°–115° C.

EXAMPLE 15 COMPOUND P

Sodium bicarbonate (8 g) and a solution of ethyl 3-chloroformylpropionate (2.5 g) in dry acetone (30 ml), the latter in a dropwise manner, were added with stirring to a solution of spiramycin mixture (8.4 g) in dry acetone (80 ml). The mixture was stirred for 5 hours and was then left to stand for 18 hours. The solid was filtered off and the filtrate was evaporated under reduced pressure. The residue was dissolved in aqueous acetic acid solution (75 ml; 0.5 N) and the resulting mixture was extracted with ethyl acetate (2×50 ml) and then with chloroform (2×50 ml). The combined chloroform extracts were washed with water (100 ml) and 5% w/v aqueous sodium bicarbonate solution (100 ml), and dried over magnesium sulphate. The chloroform was removed under reduced pressure to give the 2'-ethyl succinate of spiramycin mixture (4.4 g), m.p. 80°–90° C.

The spiramycin mixture used in the foregoing preparative example comprised approximately 60% w/w spiramycin I, 20% w/w spiramycin II and 20% w/w spiramycin III.

EXAMPLE 16 COMPOUND Q

A solution of hydrogen chloride in ethanol was added dropwise to a solution of 2'-ethyl succinate of spiramycin I (1.5 g) in diethyl ether (50 ml) until no more solid was precipitated. The white solid was filtered off, washed with diethyl ether and dried to give the dihydrochloride of the 2'-ethyl succinate of spiramycin I (1.4 g), m.p. 64°–74° C.

EXAMPLE 17 COMPOUND R

A saturated solution of oxalic acid in diethyl ether was added dropwise to a solution of 2'-ethyl succinate of spiramycin I (1.5 g) in diethyl ether (50 ml) until no more solid was precipitated. The white solid was filtered off, washed with diethyl ether and dried to give the dioxalate salt of 2'-ethyl succinate of spiramycin I (1.6 g), m.p. 85°–97° C.

The present invention includes within its scope pharmaceutical compositions which comprise at least one compound of general formula I together with a compatible pharmaceutically-acceptable carrier or coating. The compounds of general formula I will normally be administered rectally, vaginally, parenterally or, more especially, orally.

Solid compositions for oral administration include compressed tablets, pills, dispersible powders, and granules. In such solid compositions one or more of the active compounds is, or are, admixed with at least one inert diluent such as mannitol, calcium carbonate, potato starch, alginic acid or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Compositions for oral administration include granules, formulated in manner known per se, such manner being defined as a manner heretofore used or described in the literature, which may be dispersed in water before use.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment. In the adult human, the doses may be between 0.1 and 10 g/day, but are generally of 1 to 4 g/day, by oral administration for the treatment of bacterial infections.

The following Examples illustrate pharmaceutical compositions according to the invention:

EXAMPLE 18

Tablets having the following composition are prepared by the usual technique:

| | |
|---|---|
| 2'-ethyl glutarate of spiramycin I | 0.250 g |
| starch | 0.150 g |
| colloidal silica | 0.070 g |
| magnesium stearate | 0.030 g. |

EXAMPLE 19

Granules having the following composition are prepared by the usual technique:

| | |
|---|---|
| 2'-ethyl glutarate of spiramycin I | 5% w/w |
| mannitol | 95% w/w |

According to a further feature of the present invention, there are provided compositions suitable for administration to animals and birds, including concentrates for addition to their feedstuff or drinking water, comprising at least one compound of general formula I, in association with a physiologically innocuous carrier. By the expression 'physiologically innocuous carrier' as used herein is meant a carrier which is not harmful to the animal or bird. The carrier may be solid or semi-solid or a liquid. Such compositions are conveniently produced by intimately dispersing the active ingredient through the carrier, if necessary, where the carrier is a liquid in which the active substance is but sparingly soluble, e.g. water, using an emulsifying, dispersing, suspending or wetting agent.

Preferred compositions are solid or semi-solids in which the carrier is provided at least in part by a feedstuff, i.e., an organic or mineral substance which is intended to be fed to the animal or bird; that is to say, the active ingredient may be incorporated in a solid or semi-solid feedstuff. Thus, another aspect of the invention is a feedstuff comprising, in an effective amount, at least one compound of formula I. Incorporation of the active ingredient in the feedstuff may be effected by any conventional method such as stirring, tumbling or grinding. Compositions of varying concentrations can be prepared by altering the ratio of carrier to active ingredient. The active ingredient may also be incorporated in the feedstuff in the form of a powder concentrate containing active ingredient and a solid, physiologically innocuous carrier, e.g. wheat middlings, talc, kaolin or chalk or a diatomaceous earth, such as kieselguhr, or a mixture thereof, and such compositions are also included within the scope of this invention. These compositions may also contain agents to promote adhesion of the active ingredient to the carrier, for example soya oil. To the active ingredient or compositions containing it, there may be added before admixture with the feedstuff, one or more physiologically innocuous wetting and/or dispersing agents, for example, the condensation product of $\beta$-naphthalenesulphonic acid and formaldehyde, sodium lauryl sulphate or polyoxyethylene (20) sorbitan monooleate. Alternatively, when a wetting, suspending, emulsifying or dispersing agent is added to the active ingredient or powder, the composition so obtained may be mixed with water to provide stable dispersions suitable for addition to feedstuffs.

Compositions suitable for addition to feedstuffs which comprise the active substance in association with a wetting, suspending, dispersing or emulsifying agent, with or without a physiologically innocuous carrier, are also included within the scope of this invention.

The compositions of the invention may, if desired, also contain one or more prophylactic or therapeutic agents, for example antibacterials, antibiotics, anthelmintics, anti-fluke drugs and coccidiostats, as well as nutritional additives such as vitamins and mineral salts. Suitable prophylactic and therapeutic agents and nutritional additives are well known in the art and may be selected as desired, provided that they are compatible with the compound or compounds of general formula I and with the other components of the compositions of the invention in which they are to be used.

Liquid compositions may be dispersions of the active ingredient in drinking water, and these compositions may be prepared from concentrates which may be added to water or are self-emulsifying with water. Such concentrates comprise the active ingredient in association with a wetting, suspending, dispersing or emulsifying agent, with or without a physiologically innocuous carrier, or in association with a water-soluble physiologically innocuous carrier, and are included within the scope of this invention. Examples of these concentrates are:

(1) Mixtures of the active ingredient with a wetting or dispersing agent;
(2) Powders comprising the active ingredient, a physiologically innocuous carrier, and a wetting, suspending or dispersing agent;
(3) Stable dispersions obtained by mixing concentrates of types (1) or (2) with water; and
(4) Mixtures of the active ingredient with a water-soluble physiologically innocuous carrier, e.g. sucrose or glucose.

It is also possible to administer the compounds of the present invention orally in the form of granules, pellets, suspensions, solutions and emulsions comprising the active ingredient in association with suitable physiologically innocuous carriers and adjuvants. Such administration is, however, generally less convenient and therefore such compositions are not preferred.

The compounds of general formula I are administered to the animals and birds at such a rate as may be decided by the farmer, veterinarian, or other person skilled in the art having regard to the species, age, size, sex and condition of the animals and birds, generally at such a rate as to represent between, for example, 5 and 50 mg per kg of feed consumed. As mentioned above, the compounds may be administered via the drinking water or the solid or semi-solid feed.

It will be appreciated that when concentrates in the form of pellets or granules are employed as the means of administration of the active compounds of general formula I the proportion of active compound present in the pellets or granules themselves is considerably higher than the above-mentioned proportions suitable in feedstuffs and that the concentrates can be distributed throughout a feedstuff so as to give, on average over the whole of the feed, an amount of 5 to 50 mg of active compound per kg of feed.

The following Example illustrates a growth-promoting composition according to the invention.

EXAMPLE 20

Composition of a foodstuff for pigs

| | |
|---|---|
| barley | 71 kg |
| maize | 10 kg |
| soya cake (containing 50% of proteins) | 15 kg |
| vitamin-containing mineral compound | 4 kg |
| 2'-ethyl glutarate of spiramycin I | 2 g |

We claim:
1. A spiramycin derivative of the formula:

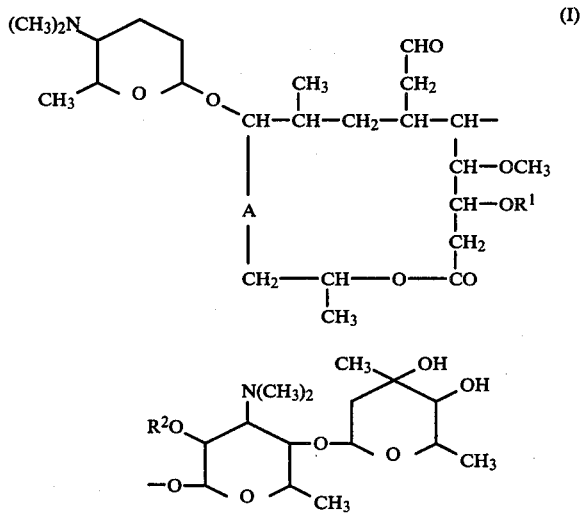

wherein $R^1$ represents acetyl, propionyl or hydrogen, A represents butenylene or butadienylene (wherein any double bonds present in A are trans), and $R^2$ represents a group of the formula:

wherein Z represents bivalent saturated or unsaturated alkylene of 1 to 6 carbon atoms, Y represents sulphur or oxygen, and $R^3$ represents alkyl of 1 to 6 carbon atoms, cycloalkyl of 3 to 8 carbon atoms, phenyl or phenylalkyl in which the alkylene moiety is of 1 to 6 carbon atoms.

2. A spiramycin derivative according to claim 1 wherein $R^3$ in the group of formula II depicted in claim 1 is other than phenyl.

3. A spiramycin derivative according to claim 1 wherein $R^1$ represents hydrogen.

4. A spiramycin derivative according to claim 1 wherein A represents butadienylene wherein the double bonds are trans.

5. A spiramycin derivative according to claim 1 wherein $R^2$ represents a group of formula II depicted in claim 1 wherein Y represents oxygen and $R^3$ represents alkyl of 1 to 3 carbon atoms.

6. A spiramycin derivative according to claim 1 wherein $R^2$ represents a group of formula II wherein Z represents ethylene or trimethylene, Y represents oxygen and $R^3$ represents alkyl of 1 to 3 carbon atoms.

7. A spiramycin derivative according to claim 6 wherein $R^3$ represents ethyl.

8. The spiramycin derivative according to claim 1 which is 2'-ethyl succinate of spiramycin I.

9. The spiramycin derivative according to claim 1 which is 2'-ethyl glutarate of spiramycin I.

10. The spiramycin derivative according to claim 1 which is 2'-methyl succinate of spiramycin I.

11. The spiramycin derivative according to claim 1 which is 2'-propyl succinate of spiramycin I.

12. The spiramycin derivative according to claim 1 which is 2'-methyl glutarate of spiramycin I.

13. The spiramycin derivative according to claim 1 which is 2'-methyl fumarate of spiramycin I.

14. The spiramycin derivative according to claim 1 which is 2'-S-methyl thiosuccinate of spiramycin I.

15. The spiramycin derivative according to claim 1 which is 2'-cyclohexyl succinate of spiramycin I.

16. The spiramycin derivative according to claim 1 which is 2'-ethyl malonate of spiramycin I.

17. The spiramycin derivative according to claim 1 which is 2'-phenyl succinate of spiramycin I.

18. The spiramycin derivative according to claim 1 which is 2'-methyl (RS)-(3-methyl) succinate of spiramycin I.

19. The spiramycin derivative according to claim 1 which is 2'-(2-phenylethyl) succinate of spiramycin I.

20. The spiramycin derivative according to claim 1 which is 2'-tertiary-butyl succinate of spiramycin I.

21. The spiramycin derivative according to claim 1 which is 2'-isopropyl succinate of spiramycin I.

22. Dihydrochloride of the spiramycin derivative according to claim 1 which is 2'-ethyl succinate of spiramycin I.

23. Dioxalate of the spiramycin derivative according to claim 1 which is 2'-ethyl succinate of spiramycin I.

24. Acid addition salts of a spiramycin derivative claimed in claim 1.

25. A mixture of derivatives according to claim 1 which is a mixture of the 2'-ethyl succinates of a spiramycin mixture containing approximately 60% w/w spiramycin I, 20% w/w spiramycin II and 20% w/w spiramycin III.

26. A mixture of spiramycin derivatives each of which is a spiramycin derivative according to claim 1, the said derivatives differing only in respect of the symbol $R_1$ and being identical in respect of A and $R_2$.

27. A pharmaceutical antibiotic composition which comprises a therapeutically effective amount of spiramycin derivative as claimed in claim 1 or a non-toxic pharmaceutically acceptable acid addition salt thereof together with a compatible pharmaceutically acceptable carrier.

28. A composition suitable for administration to animals and birds, including a concentrate for addition to their feedstuff or drinking water, comprising a growth promoting amount of spiramycin derivative as claimed in claim 1 or a non-toxic acid addition salt thereof in association with a physiologically innocuous carrier.

29. Compositions according to claim 28 in which the carrier is a feedstuff and the composition contains 5 to 50 mg of active compound per kg of feedstuff.

* * * * *